United States Patent [19]

Dutton et al.

[11] Patent Number: 5,057,498

[45] Date of Patent: Oct. 15, 1991

[54] ANTIPARASTIC AGENTS

[75] Inventors: Christopher J. Dutton, Sandwich; Stephen P. Gibson, Margate; Nigel D. A. Walshe, Deal, all of England

[73] Assignee: Pfizer Inc., New York, N.Y.

[21] Appl. No.: 575,039

[22] Filed: Aug. 29, 1990

Related U.S. Application Data

[62] Division of Ser. No. 371,461, Jun. 26, 1989, Pat. No. 4,980,370.

[30] Foreign Application Priority Data

Jul. 5, 1988 [GB] United Kingdom ................ 8815967

[51] Int. Cl.$^5$ .................... A61K 31/335; A61K 31/70
[52] U.S. Cl. ........................................ 514/30; 530/7.1; 514/450
[58] Field of Search .................... 514/450, 30; 536/7.1

[56] References Cited

U.S. PATENT DOCUMENTS 4,328,335  5/1982  Mrozik ................................ 536/7.1
4,423,209 12/1983  Mrozik ................................ 536/7.1

FOREIGN PATENT DOCUMENTS 1689    6/1979  European Pat. Off. .
2615    6/1979  European Pat. Off. .
170006  2/1986  European Pat. Off. .
214731  3/1987  European Pat. Off. .
276103  7/1988  European Pat. Off. .
276131  7/1988  European Pat. Off. .
317148  5/1989  European Pat. Off. .
1390336 6/1973  United Kingdom .
1573955 8/1980  United Kingdom .

OTHER PUBLICATIONS

Cane, D. E. et al., J. Amer. Chem. Soc. 109, 1255–1257 (1987).
Hutchinson, R. C. et al., J. Amer. Chem. Soc. 109, 1253–1255 (1987).
Meinwald, J. et al., J. Amer. Chem. Soc. 85, 582–585 (1963).
Robinson, J. A. et al., J. Chem. Soc., Chem. Comm. 1988, 4–6.

*Primary Examiner*—C. Warren Ivy
*Assistant Examiner*—Amelia A. Owens
*Attorney, Agent, or Firm*—Peter C. Richardson; J. Trevor Lumb; A. Dean Olson

[57] ABSTRACT

Antiparasitic compounds of formula (I):

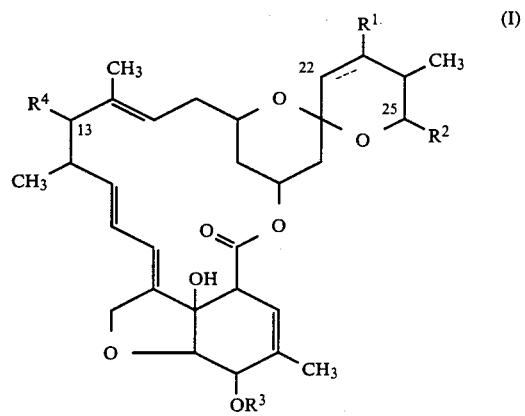

The broken line at the 22–23 position representing an optional double bond and either $R^1$ is H or OH and the double bond is absent or the double bond is present and $R^1$ is absent; $R^2$ is optionally substituted phenyl, or a group of formula (II):

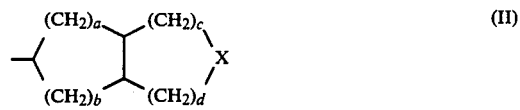

wherein
X is O, S or —$CH_2$13 , abc and d are 0–2 and $a+b+c+d \leq 5$
$R^3$ is H or Me
$R^4$ is H, OH or 4'-(alpha-L-oleandrosyl)-alpha-L-oleandrosyloxy.

The compounds are prepared by fermentation of *Streptomyces avermitilis* in the presence of an N-alkanoyl cysteamine thioester containing $R^2$.

2 Claims, No Drawings

ANTIPARASTIC AGENTS

This is a division of application Ser. No. 07/371,461, filed on June 26, 1989, U.S. Pat. No. 4,980,370.

BACKGROUND OF THE INVENTION

This invention relates to antiparasitic agents and in particular to compounds related to the avermectins and milbemycins, but having a novel substituent group at the 25-position and to a process for their preparation.

The avermectins are a group of broad spectrum antiparasitic agents referred to previously as the C-076 compounds. They are produced by fermenting a strain of the microorganism *Streptomyces avermitilis* ATCC 31267, 31271 or 31272 under aerobic conditions in an aqueous nutrient medium containing inorganic salts and assimilable sources of carbon and nitrogen. The morphological and cultural properties of the strains ATCC 31267, 31271 and 31272 are described in detail in British Patent Specification No. 1573955 which also describes the isolation and the chemical structure of the eight individual components which make up the C-076 complex.

The milbemycins are structurally related macrolide antibiotics lacking the sugar residues at the 13-position. They may be produced by fermentation, for example, as described in British Patent Specification 1390336 and European Patent Application 170006.

The aglycones are derivable from the avermectins by hydrolysis to remove the sugar residues to produce a similar compound having a hydroxy group at the 13-position.

In our European Patent Application publication No. 0214731 we disclose that by adding certain specified carboxylic acids, or derivatives thereof, to the fermentation of an avermectin producing organism it is possible to obtain novel compounds, related to the avermectins but having an unnatural substituent group at the 25-position in place of the isopropyl or sec-butyl group which is normally present.

The novel compounds produced are characterised in that the substituent group at the 25-position is alpha-branched i.e. the carbon atom attached to the C-25 ring position is a secondary carbon atom linked to two further carbon atoms.

In our co-pending European patent application Nos. 88.300354.3 and 88300426.9 we describe and claim new mutant strains of the microorganism *Streptomyces avermitilis* lacking branched-chain 2-oxo acid dehydrogenase activity. Said strains have been deposited in the American Type Culture Collection, Rockville, Md. under the designations *Streptomyces avermitilis* ATCC 53567, ATCC 53568 and ATCC 53692. In our British patent application 87.26730 we disclose that, by using these new mutant strains of *Streptomyces avermitilis* it is possible to obtain a further range of novel avermectin derivatives, not previously obtainable, wherein the C-25 substituent is linked by an unbranched (primary) carbon atom. These avermectins are prepared by fermenting the afore-mentioned microorganisms in the presence of the appropriate carboxylic acid or a salt, ester or amide thereof or oxidative precursor therefor. It has now been discovered that certain carboxylic acids, which do not incorporate when added to the fermentation as the free carboxylic acid or a simple ester or thioester, will produce novel avermectins if added in the form of an N-alkanoyl crsteamine thioester.

N-alkanoyl cysteamine thioesters have been used in biosynthetic studies for other purposes, see R. C. Hutchinson et. al., J. Amer. Chem. Soc., 1987, 109, 1253-1255 or D. E. Cane et. al., J. Amer. Chem. Soc., 1987, 109, 1255-1257 or J. A. Robinson et. al., J. Chem. Soc., Chem. Comm. 1988, 4.

SUMMARY OF THE INVENTION

The novel compounds so produced are active antiparasitic agents having particular utility as anthelmintics, ectoparasiticides, insecticides, acaricides and animal growth promoting agents. The compounds can be subjected to conventional chemical transformation reactions to obtain further novel semi-synthetic derivatives. Thus, according to one aspect of the present invention there are provided compounds having the formula (I):

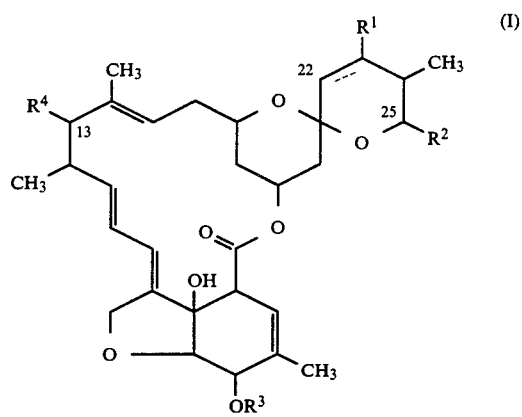

wherein
the broken line at the 22-23 position represents an optional double bond and wherein either $R^1$ is H or OH and the double bond is absent, or, the double bond is present and $R^1$ is absent;

$R^2$ is phenyl which may optionally be substituted with at least one substituent selected from $C_1$-$C_4$ alkyl, $C_1$-$C_4$ alkoxy and $C_1$-$C_4$ alkylthio groups, halogen atoms, trifluoromethyl, and cyano; or $R^2$ may be a group of formula (II):

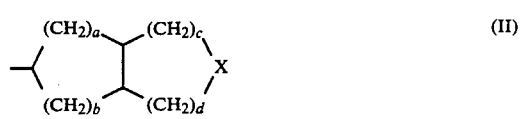

wherein
X is O, S or —$CH_2$— and a, b, c and d may each independently be 0, 1 or 2; the sum of a, b, c and d not exceeding 5;

$R^3$ is hydrogen or methyl; and $R^4$ is H, OH or a 4'-(alpha-L-oleandrosyl)-alpha-L-oleandrosyloxy group of the formula:

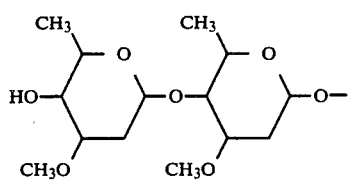

In the above definition, alkyl groups containing 3 or more carbon atoms may be straight or branched chain. Halo means fluoro, chloro, bromo or iodo.

The C-076 complex comprises eight distinct but closely related compounds described as C-076 A1a, A1b, A2a, A2b, B1a, B1b, B2a and B2b. The "a" series of compounds refers to the natural avermectin wherein the 25-substituent is (S)-sec-butyl and the "b" series to those wherein the 25-substituent is isopropyl. The designations "A" and "B" refer to avermectins wherein the 5-substituent is methoxy or hydroxy, respectively, and the numeral "1" refers to avermectins wherein a double bond is present at the 22-23 position, and numeral "2" to avermectins having a hydrogen at the 22-position and hydroxy at the 23 position.

In this application, the "a" and "b" identifiers have been dropped. Identifiers A1, A2, B1 and B2 have been retained to refer to non-natural avermectins having the structural features corresponding to those of the C-076 avermectins as noted above.

The invention includes compounds of the formula (I) wherein $R^2$ is phenyl.

In another group of compounds, $R^2$ is a group of formula (II) wherein
a and b are 0;
c and d are 1; and
X is $CH_2$.

In a further group of compounds, $R^2$ is a group of formula (II) wherein
a and b are 0;
c is 1;
d is 2; and
X is $CH_2$.

In yet another group of compounds, $R^2$ is a group of formula (II) wherein
a and b are 0;
c and d are 1; and
X is 0.

The especially preferred compounds are 25-phenyl avermectin B2 and 25-(2-bicyclo[3.1.0]hexyl)avermectin B2.

The invention also includes a process for preparing a compound of formula (I) as claimed in claim 1, which comprises fermenting a *Streptomyces avermitilis* mutant organism ATCC 53567, 53568 or 53692 in the presence of an N-alkanoyl cysteamine thioester of formula (III):

$$R^2COS(CH_2)_2NHCOR^6$$

wherein $R^2$ is as defined as above and $R^6$ is a $C_1-C_{10}$ alkyl group, and isolating the compound of formula (I) wherein $R^1$ is OH and the double bond is absent, or wherein the double bond is present and $R^1$ is absent, and $R^4$ is 4'-(alpha-L-oleandrosyl)-alpha-L-oleandrosyloxy, followed if necessary by one or more of the following steps:

(i) subjecting said compound in which the double bond is absent and $R^1$ is OH to dehydration, and hydroxy groups at the 5 and $4^{11}$ positions being selectively protected during the dehydration, to yield a compound of formula (I) in which the double bond is present and $R^1$ is absent, (ii) demethylating said compound in which $R^3$ is methyl to produce a compound of formula (I) in which $R^3$ is H, (iii) subjecting said compound in which the double bond is present to selective catalytic hydrogenation to yield a compound of formula (I) in which the double bond is absent and $R^1$ is H, (iv) hydrolysing said compound in which $R^4$ is 4'-(alpha-L-oleandrosyl)-alpha-4-oleandrosyloxy to yield a compound of formula (I) in which $R^4$ is OH, (v) halogenating a compound obtained from step (iv) to yield a 13-deoxy-13-halo derivative and selectively reducing said derivative to yield a compound of formula (I) in which $R^4$ is H.

The present invention also includes a composition for the treatment and prevention of parasitic infections in humans and animals, including ectoparasiticidal, insecticidal, acaricidal and anthelmintic compositions, which comprises a compound of formula (I) with an inert diluent or carrier. Especially preferred within this composition is a composition in the form of a liquid drench or an oral or injectable formulation, or in the form of an animal feedstuff or premix or supplement for addition to animal feed.

Finally, the present invention includes a method of combating insect or parasitic infections or infestations, including parasitic conditions in humans and animals and agricultural or horticultural pest infestations, which comprises applying an insecticidal or antiparasitic effective amount of a compound of formula (I) to the organism responsible for said infection or infestation or to the location thereof.

DETAILED DESCRIPTION OF THE INVENTION

Compounds of formula (I) wherein $R^1$ is OH and the double bond is absent or wherein the double bond is present and $R^1$ is absent and $R^4$ is 4'-(alpha-L-oleandrosyl)-alpha-L-oleandrosyloxy are prepared by fermenting a *Streptomyces avermilitis* mutant organism ATCC 53567, 53568 or 53692, as described in European patent applications 88300354.3 and 88300426.9 in the presence of the appropriate N-alkanoyl cysteamine thioester of the formula (III).

$$R^2COS(CH_2)_2NHCOR^6 \qquad (III)$$

wherein $R^2$ is as defined above, and $R^6$ is $C_1-C_{10}$ alkyl group. The thioester is added to the fermentation either at the time of inoculation or at intervals during the fermentation. Production of the compounds of formula (I) may be monitored by removing samples from the fermentation, extracting with an organic solvent and following the appearance of the compound of formula (I) by chromatography, for example using high pressure liquid chromatography. Incubation is continued until the yield of the compound of formula (I) has been maximised, generally for a period of from 12 to 16 days.

A preferred level of each addition of the thioester is between 0.05 and 4.0 grams per liter. The best yields of the compounds of formula (I) are obtained by gradually adding the acid to the fermentation, for example by daily additions of the thioester over a period of several days. The medium used for the fermentation may be a conventional complex medium containing assimilable sources of carbon, nitrogen and other trace elements.

After fermentation for a period of several days at a temperature preferably in the range of from 24° to 33° C., the fermentation broth is centrifuged or filtered and the mycelial cake is extracted with acetone or methanol. The solvent extract is concentrated and the desired product is then extracted into a water-immiscible organic solvent, such as methylene chloride, ethyl acetate, chloroform, butanol or methyl isobutyl ketone. The solvent extract is concentrated and the crude product containing the compounds of formula (I) is further purified as necessary by chromatography, for example using preparative reverse phase, high pressure liquid chromatography.

The product is generally obtained as a mixture of the compounds of formula (I) wherein $R^4$ is 4'-(alpha-L-oleandrosyl)-alpha-L-oleandrosyloxy, $R^1$ is OH and the double bond absent or $R^1$ is absent and the double bond is present and wherein $R^3$ is H or $CH_3$; however the proportions can vary depending on the particular thioester employed and the conditions used in the fermentation. When the micro-organism used is ATCC 57692 only the B-type avermectin in which $R^3$ is H is obtained.

It has been found that a range of thioesters as described by formula (III) may be added to the fermentation to yield avermectins having a range of substituent groups at the C-25 position. Examples of particular thioesters which may be employed include the following:

A thioester of formula (III), in which $R^2$ is phenyl and $R^6$ is methyl;

A thioester of formula (III) in which $R^2$ is a group as defined in formula (II) in which a and b are 0, c and d are 1 and X is $CH_2$, and $R^6$ is methyl;

A thioester of formula (III) in which $R^2$ is a group as defined in formula (II) in which a and b are 0, c is 1, d is 2 and X is $CH_2$ and $R^6$ is methyl;

and a thioester of formula (III) in which $R^2$ is a group as defined in formula (II) in which a and b are 0, c and d are 1 and X is O and $R^6$ is methyl.

In one particular and preferred aspect of the invention, the fermentation is performed in the presence of a thioester of formula (III) in which $R^2$ is phenyl and $R^6$ is methyl, to yield predominantly the compound of formula (I) wherein $R^1$ is OH and the double bond is absent, $R^2$ is phenyl, $R^3$ is H and $R^4$ is 4'-(alpha-L-oleandrosyl)-alpha-4-oleandrosyloxy, referred to herein as 25-phenyl avermectin B2.

In another preferred aspect of the invention, the fermentation is performed in the presence of a thioester of formula (III) in which $R^2$ is 2-bicyclo[3.1.0]hexyl and $R^6$ is methyl, to yield predominantly the compound of formula (I) wherein $R^1$ is OH and the double bond is absent, $R^2$ is 2-bicyclo[3.1.0]hexyl, $R^3$ is H and $R^4$ is 4'-(alpha-L-oleandrosyl)-alpha-4-oleandrosyloxy, referred to herein as 25-(2-bicyclo[3.1.0]hexyl)avermectin B2.

Thioesters of formula (III) may be prepared from the corresponding carboxylic acids of the formula $R^2-CO_2H$ by coupling with a thiol of the formula $R^6CONHCH_2CH_2SH$ in the presence of a dehydrating agent such as dicyclohexylcarbodiimide in an inert solvent or using diphenylphosphorylazide and a base such as triethylamine in dimethylformamide. Thiols of the formula $R^6CONHCH_2CH_2SH$ may be prepared from cysteamine hydrochloride by treatment with a base such as triethylamine followed by trimethylsilyl chloride then an acid chloride of the formula $R^6COCl$ and a further amount of a base such as triethylamine. The resulting crude thioester is then purified by, for example, column chromatography on silica gel.

Carboxylic acids of the formula $R^2CO_2H$ in which $R^2$ is a group of formula (II), wherein a and b are 0, and c, d and X are as previously defined may be prepared by the addition of alkyl diazoacetate esters to cycloalkenes of the formula

$$CH = CH(CH_2)_cX(CH_2)_d$$

in the presence of rhodium (II) acetate, followed by cleavage of the resultant alkyl esters.

The resultant carboxylic acid may then be purified by conventional means, for example distillation or crystallization.

Preparation of bicyclo[3.1.0]hexane-2-carboxylic acid is described in J. Amer. Chem. Soc., 85, 582–585, 1963 (Meinwald J., Labana S. S., Chadha M. S.).

Compounds of the formula (I) wherein the double bond is present and $R^1$ is absent may alternatively be prepared from the corresponding compound of formula (I) wherein $R^1$ is OH and the double bond is absent by a dehydration reaction. The reaction is performed by first selectively protecting the hydroxyl groups at the 5 and 4" positions, e.g. as the t-butyldimethylsilyloxy acetyl derivative, then reacting with a substituted thiocarbonyl halide, such as (4-methylphenoxy)thiocarbonyl chloride, followed by heating in a high boiling point solvent, e.g. trichlorobenzene, to effect the dehydration. The product is finally deprotected to give the unsaturated compound. These steps together with appropriate reagents and reaction conditions are described in U.S. Pat. No. 4,328,335.

The compounds of formula I wherein $R^3$ is H may also be prepared from the corresponding compounds wherein $R^3$ is $CH_3$ by demethylation. This reaction is achieved by treating the 5-methoxy compound, or a suitably protected derivative thereof, with mercuric acetate and hydrolysing the resulting 3-acetoxy enol ether with dilute acid to give the 5-keto compound. This is then reduced using, for example, sodium borohydride to yield the 5-hydroxy derivative. Appropriate reagents and reaction conditions for these steps are described in U.S. Pat. No. 4,423,209.

The compounds of formula I wherein $R^1$ is H and the double bond is absent can be prepared from the corresponding compound wherein the double bond is present and $R^1$ is absent, by selective catalytic hydrogenation using an appropriate catalyst. For example the reduction may be achieved using tris(triphenylphosphine)rhodium (I) chloride as described in European patent application publication No. 0001689.

The compounds of formula (I) wherein $R^4$ is H may be prepared from the corresponding compounds wherein $R^4$ is 4'-(alpha-L-oleandrosyl)-alpha-L-oleandrosyloxy by removing the 4'-(alpha-L-oleandrosyl)-alpha-L-oleandrose group by mild hydrolysis with an acid in an aqueous organic solvent to yield the aglycone wherein $R^4$ is OH; this is then halogenated, for example by reacting with a benzene sulphonyl halide, to yield the 13-deoxy-13-halo derivative which is finally selectively reduced, for example using tributyltin hydride. In order to avoid unwanted side reactions it is desirable to protect any other hydroxy groups which may be present, for example using a tert-butyldimethylsilyl group. This is then readily removed after the halogenation or reduction step by treatment with methanol containing a trace of acid. All these steps together with appropriate reagents and reaction conditions for their performance are described in European patent application publication No. 002615.

The compounds of the invention are highly active antiparasitic agents having particular utility as anthelmintics, ectoparasiticides, insecticides, acaricides, and animal growth promoters.

Thus the compounds are effective in treating a variety of conditions caused by endoparasites including, in particular, helminthiasis which is most frequently caused by a group of parasitic worms described as nematodes and which can cause severe economic losses in swine, sheep, horses and cattle as well as affecting domestic animals and poultry. The compounds are also effective against other nematodes which affect various species of animals including, for example, Dirofilaria in dogs and various parasites which can infect humans including gastro-intestinal parasites such as Ancylostoma, Necator, Ascaris, Strongyloides, Trichinella, Capillalria, Trichuris, Enterobius and parasites which are found in the blood or other tissues and organs such as filiarial worms and the extra intestinal stages of Strongyloides and Trichinella.

The compounds are also of value in treating ectoparasite infections including in particular arthropod ectoparasites of animals and birds such as ticks, mites, lice, fleas, blowfly, biting insects and migrating dipterous larvae which can affect cattle and horses.

The compounds are also insecticides active against household pests such as the cockroach, clothes moth, carpet beetle and the housefly as well as being useful against insect pests of stored grain and of agricultural plants such as spider mites, aphids, caterpillars, fire ants, termites and against migratory orthopterans such as locusts.

The compounds of formula (I) are administered as a formulation appropriate to the specific use envisaged and to the particular species of host animal being treated and the parasite or insect involved. For use as an anthelmintic the compounds may be administered orally in the form of a capsule, bolus, tablet or preferably a liquid drench, or alternatively, they may be administered by injection or as an implant or as a pour-on formulation. Such formulations are prepared in a conventional manner in accordance with standard veterinary practice. Thus capsules, boluses or tablets may be prepared by mixing the active ingredient with a suitable finely divided diluent or carrier, additionally containing a disintegrating agent and/or binder such as starch, lactose, talc, magnesium stearate etc. A drench formulation may be prepared by dispersing the active ingredient in an aqueous solution together with dispersing or wetting agents etc. and injectable formulations may be prepared in the form of a sterile solution which may contain other substances, for example, enough salts or glucose to make the solution isotonic with blood. These formulations will vary with regard to the weight of active compound depending on the species of host animal to be treated, the severity and type of infection and the body weight of the host. Generally for oral administration a dose of from about 0.001 to 10 mg per Kg of animal body weight given as a single dose or in divided doses for a period of from 1 to 5 days will be satisfactory but of course there can be instances where higher or lower dosage ranges are indicated and such are within the scope of this invention.

As an alternative the compounds may be administered with the animal feedstuff and for this purpose a concentrated feed additive or premix may be prepared for mixing with the normal animal feed.

For use as an insecticide and for treating agricultural pests the compounds are applied as sprays, dusts, emulsions and the like in accordance with standard agricultural practice.

For use as a growth promotant or for improving the lean meat to fat ratio in farm or domestic animals, the compounds may be administered with the animal feedstuff or drinking water. Alternatively, they may be administered orally in the form of a capsule, bolus, tablet or liquid drench, or parenterally by injections or as an implant.

For human use the compounds are administered as a pharmaceutically acceptable formulation in accordance with normal medical practice.

The invention is illustrated by the following Examples in which Example 1 is an Example of the preparation of a compound of the formula (I) Example 2 is an example of the preparation of another compound of formula (I). Example 3 is an example of a drench formulation and Examples 4 and 5 illustrate the antiparasitic and insecticidal activity of the compounds of Examples 1 and 2.

EXAMPLE 1

25-Phenyl avermectin B2

A frozen inoculum (2 ml) of a culture of *Streptomyces avermitilis* mutant organism ATCC 53568 was inoculated into 50 mls of a medium containing starch (1 g), Pharmamedia (Trademark) (0.75 g), ardamine pH (0.25 g), and calcium carbonate (0.1 g) in a 300 ml flask and incubated at 28° C. for 2 days. This inoculum (50 ml) was transferred to a second inoculum flask (1 liter) containing starch (20 g), Pharmamedia (15 g), ardamine pH (5 g) and calcium carbonate (2 g) and incubated at 28° C. for a further 2 days. This inoculum was used to inoculate 70 liters of a medium containing starch (7 kg), magnesium sulphate (70 g), Pharmamadia (350 g), dipotassium hydrogen phosphate (70 g), ferrous sulphate (0.7 g), calcium carbonate (490 g), glutamic acid (42 g), zinc sulphate (0.07 g) and manganous sulphate (0.07 g) contained in a 70 liter fermenter. The fermentation was incubated at 28° C., with agitation at 350 r.p.m. and aeration at 70 liters per minute. S-Benzoyl N-acetyl cysteamine (24 g) was added after 24 hours. After 288 hours the mycelium was removed by filtration and extracted with acetone (2×50 liters). The acetone extract was concentrated to approximately 10 liters and extracted with ethyl acetate (30 liters) in three portions. The resulting ethyl acetate layers were combined and evaporated to give a brown oil (97.5 g).

The latter was dissolved in methylene chloride (1200 ml) and stirred with silica gel (100 g) and charcoal (100 g) for 1 hour. The silica and charcoal were removed by filtration through Arbacel and the filtrate was evaporated to give a yellow oil (74.5 g). The latter was dissolved in 100 ml petrol (b.p. 40°–60°C.) and filtered. The filtrate was added to a 500 g alumina (Woelm. Akt. B) column and eluted with petrol (b.p. 60°–80° C.), (1.5 liter), ethyl acetate (2 liters) and finally methanol (1 liter). Relevant fractions were combined to give 4.12 g of a pale brown oil. This was dissolved in methanol (200 ml) and cooled to −75° C. A waxy precipitate appeared and was filtered off. The filtrate was evaporated to give 2.98 g of a mobile oil which wa dissolved in diethyl ether and added to a column of silica gel (35 g) and eluted with diethyl ether. Fractions (100 ml) were collected and fraction numbers 13 and 20 were combined and evaporated to yield partially purified material. The product was dissolved in methanol (0.7 mm) and chromatographed on a C18 Zorbax ODS (Trademark, Dupont) column (21 mm×25 cm) eluting with a mixture of methanol and water (75:25) at a flowrate of 9 ml per minute. 4.5 ml Fractions were collected and fractions 86 to 96 were combined and evaporated to yield a compound of formula (I) wherein $R^1$ is OH, the double bond is absent, $R^2$ is phenyl, $R^3$ is H and $R^4$ is 4'-(alpha-L-oleandroxyl)-L-oleandroxyloxy, as a white powder, m.p. 150°–155° C. The structure of the product was confirmed by fast atom bombardment mass spectrometry, performed on a VG Model 7070E mass spectrometer using a sample matrix of triethylene glycol with solid sodium chloride. $(M+Na)^+$ observed at m/e 933 (theoretical 933).

Electron impact mass spectrometry was performed using a VG Model 7070F mass spectrometer. The m/e values for the principal fragments were: 343, 325, 259, 241, 231, 145, 127, 113, 111, 95 and 87.

EXAMPLE 2

25-(2-Bicyclo[3.1.0]hexyl)avermectin B2

A frozen inoculum (2 ml) of a culture of *Streptomyces avermitilis* mutant organism ATCC 53568 was inoculated into 50 mls of a medium containing starch (1 g), Pharmamedia (Trademark) (0.75 g), ardamine pH (0.25 g), and calcium carbonate (0.1 g) in a 300 ml flask and incubated at 28° C. for 2 days. This inoculum (50 ml) was transferred to a second inoculum flask (1 liter) containing starch (20 g) and incubated at 28° C. for a further 2 days. This inoculum was used to inoculate 100 liters of a medium containing starch (10 kg) magnesium sulphate (100 g), Pharmamadia (500 g), dipotassium hydrogen phosphate (100 g), ferrous sulphate (1.0 g), calcium carbonate (700 g) glutamic acid (60 g), zinc sulphate (0.1 g) and manganous sulphate (0.1 g) contained in a 100 liter fermenter. The fermentation was incubated at 28° C. with agitation at 200 r.p.m. and aeration at 80 liters per minute. The N-acetyl cysteamine thioester of bicyclo[3.1.0]hexane carboxylic acid (16 g) was added after 43 hours, and again at 115 hours (16 g). After 234 hours the mycelium was removed by filtration and extracted with acetone (2×50 liters). The acetone extract was concentrated to approximately 10 liters and extracted with ethyl acetate (3×15 liters). The resulting ethyl acetate layers were combined and evaporated to give a brown oil (67.8 g). The oil was dissolved in petroleum ether (b.p. 40°–60° C.) (250 ml) and chromatographed on alumina (340 g). Unwanted material was eluted with a mixture of ethyl acetate and dichloromethane (1:1) and the product eluted with a mixture of ethyl acetate and methanol (1:1). After evaporation a pale brown oil (17.8 g) was obtained which was re-dissolved in petroleum ether (b.p. 40°–60° C.) and chromatographed on silica gel (460 g). Unwanted materials were eluted with petroleum ether (b.p. 40°–60° C.), followed by diethyl ether. The product was eluted with a mixture of ethyl acetate and diethyl ether (1:9). After evaporation an off-white foam was obtained (1.3 g); which was dissolved in methanol (4 ml) and purified by chromatography using a C-18 Dynamax (Trademark Rainin) column (41.4 mm×25 cm), eluting with a mixture of methanol and water (80:20) at a flowrate of 60 ml/min. Relevant fractions were combined to yield a compound formula (I) wherein $R^1$ is OH, the double bond is absent, $R^2$ is 2-bicyclo[3.1.0]hexyl, $R^3$ is H and $R^4$ is 4'-(alpha-L-oleandroxyl)-L-oleandrosyloxyl as a white powder, m.p. 173°–176° C. (decomp). The structure of the product was confirmed by fast atom bombardment mass spectrometry performed on a VG Model 7070E mass spectrometer using a sample matrix of triethylene glycol with solid sodium chloride. $(M+Na)^+$ observed at m/e 937 (theoretical 937).

Electronic impact mass spectrometry was performed using a VG Model 7070F mass spectrometer. The m/e values for the principal fragments were: 608, 480, 347, 329, 263, 257, 179, 145, 127, 113, 95 and 87.

EXAMPLE 3

Drench Formulation

The product of the preceding Examples 1 and 2 were dissolved in polyethylene glycol (average molecular weight 300) to give solutions containing 400 micrograms/ml for use as drench formulations.

EXAMPLE 4

Anthelmintic Activity

Anthelmintic activity was evaluated against *Caenorhabditis elegans* using the in vitro screening test described by K. G. Simpkin and G. L. Coles in Parasitology, 1979, 79, 19. The products of Examples 1 and 2 killed 100% of the worms at a well concentration of 0.1 micrograms per ml.

EXAMPLE 5

Insecticidal Activity

Activity against the larval stage of the blowfly *Lucilia cuprina* (Q strain) is demonstrated using a standard procedure in which first instar larvae are kept in contact with filter paper treated with test compound. The test compound is first applied to the paper as an acetone solution. The treated filter papers are then placed into tubes containing 1 ml of newborn calf serum and the first instars are added. The products of Examples 1 and 2 killed 100% of the larvae when applied to the filter paper at a level of 1 milligram per square meter.

PREPARATIONS

Preparation of 5-benzoyl N-acetyl cycteamine

Crysteamine hydrochloride (50 g) in dry methylene chloride (800 ml) was treated at 0° to 5° C. with triethylamine (140 ml) and the slurry stirred for ½ hour. Trimethylsilyl chloride (72 ml) was then added with a further 100 ml of methylene chloride over a period of 20 minutes at 0° C. Stirring was continued at 0° C. for 1½ hours. Acetyl chloride (31 ml) is 100 ml methylene chloride was then added at 0°–5° C. over a period of 20 minutes, then triethylamine (61 ml) was added at the same temperature. The resulting white slurry was stirred vigorously for 2 hours at room temperature. Water (50 ml) was then added and the mixture evaporated to dryness in vacuo. The resulting white solid was treated with saturated brine (200 ml) and extracted with ethyl acetate (400 ml). The aqueous layer was then extracted again with ethyl acetate (3×40 ml) and the combined organic layers were dried over anhydrous sodium sulphate, filtered and evaporated to give N-acetyl cysteamine a pale yellow oil, which was distilled to give 27 g of clear oil B.pt. 103°–108° C./0.8 mmHg.

Benzoic acid (51.6 g) and 100 g of N-acetyl cystamine were dissolved in dimethylformamide (100 ml) and methylene chloride (300 ml). The resulting mixture was stirred under nitrogen at 0° C. and 184 ml of diphenylphosphorylazide was added slowly, followed after 5 minutes by 238 ml of triethylamine. The temperature was maintained below 10° C. The mixture was then stirred overnight at room temperature under nitrogen. The mixture was diluted with 100 ml methylene chloride and washed with 400 ml 5% aqueous citric acid, saturated dosium bicarbonate solution (400 ml) and saturated sodium chloride solution (400 ml), then dried over anhydrous sodium sulphate and concentrated to a yellow oil. The oil was applied to a 1 kg column of silica gel and eluted with 2% ethyl acetate in methylene chloride increasing to 100% ethyl acetate. Fractions 6 to 19 were combined to give 128 g of waxy solid. This was mixed with 40 g of arbacel and extracted with hexane using a soxhlet extractor.

The extract was evaporated to give 101.7 g of the title compound as a white solid. M.pt. 54°–57° C. The structure of the product was confirmed by fast atom bombardment mass spectrometry performed on a VG model 7070E mass spectrometer using a sample matrix of triethylene glycol.

A strong MH+ signal was seen at m/e 224 (theoretical 224).

Preparation of Bicyclo[3.1.0]hexane carboxylic acid, N-acetyl cysteamine thioester Bicyclo[3.1.0]hexane carboxylic acid (1.1 g), diphenylphosphorylazide (4.9 g) and N-acetyl cysteamine (2 g) were stirred in dimethylformamide (5 ml) at 0° C. Triethylamine (5 ml) was added dropwise and stirring was continued at ambient temperature for 24 hours. The reaction mixture was diluted with toluene (100 ml) and the solution washed with 5% aqueous citric acid (100 ml), saturated sodium bicarbonate solution (100 ml) and finally, saturated brine (100 ml). Then the organic layer was separated, dried over sodium sulphate, filtered and evaporated. The residue (2.2 g) was purified by chromatography on silica (50 g), eluting with methylene chloride and ethyl acetate (a gradient of ethyl acetate from 2 to 40%). The fractions were analysed by thin layer chromatography and fractions 13 to 20 were combined to give the product as an oil (1.2 g).

The structure of the product was confirmed by electron impact mass spectrometry using a VG Model 7070 F mass spectrometer. The m/e value for the molecular ion was 227 (theoretical 227) and the principal fragments were: 184, 168, 119, 109 and 81.

We claim:

1. A method of combating insect or parasitic infections or infestations, including parasitic conditions in humans and animals which comprises administering an insecticidal or antiparasitic effective amount of a compound of formula (I)

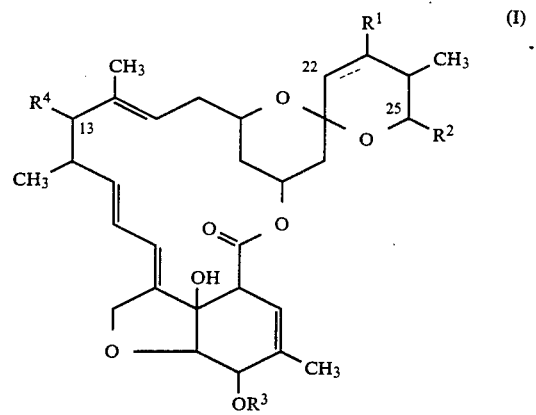

wherein the broken line at the 22–23 position represents an optional double bond; $R^1$ is hydrogen or hydroxy; $R^2$ is phenyl, substituted phenyl where said substituent is alkyl having one to four carbon atoms, alkoxy having one to four carbon atoms, alkoxy having one to four carbon atoms, alkylthio having one to four carbon atoms, chloro, fluoro, trifluoromethyl or cyano or a group of the formula $$\underset{(CH_2)_b}{\overset{(CH_2)_a}{\diagup}} \underset{(CH_2)_d}{\overset{(CH_2)_c}{\diagdown}} X \qquad (II)$$

where X is O or —CH$_2$— and a, b, c and d are each 0 to 2 such that the sum of a, b, c and d does not exceed 5; $R^3$ is hydrogen or methyl; and $R^4$ is hydrogen, hydroxy or a 4'-(alpha-L-oleandrosyl)alpha-L-oleandrosyloxy group of the formula with the proviso that when the double bond is present at the 22–23 position $R^1$ is hydrogen to the organism responsible for said infection or infestation or to the location thereof.

2. A method of combating insect or parasitic infections or infestations, including agricultural or horticultural pest infestations, which comprises applying an insecticidal or antiparasitic effective amount of a compound of formula (I)

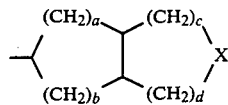

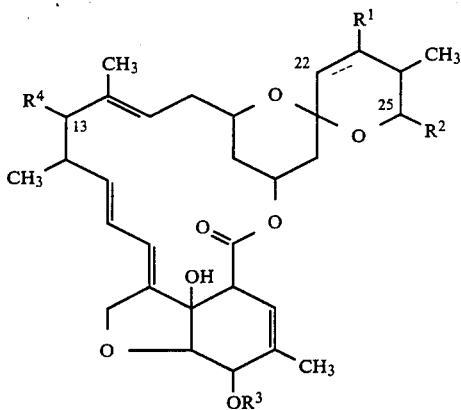 (I)

wherein the broken line at the 22-23 position represents an optional double bond; $R^1$ is hydrogen or hydroxy; $R^2$ is phenyl, substituted phenyl where said substituent is alkyl having one to four carbon atoms, alkoxy having one to four carbon atoms, alkylthio having one to four carbon atoms, chloro, fluoro, trifluoromethyl or cyano or a group of the formula

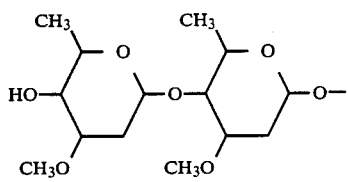 (II)

where X is O or $-CH_2-$ and a, b, c and d are each 0 to 2 such that the sum of a, b, c and d does not exceed 5; $R^3$ is hydrogen or methyl; and $R^4$ is hydrogen, hydroxy or a 4'-(alpha-L-oleandrosyl)alpha-L-oleandrosyloxy group of the formula with the proviso that when the double bond is present at the 22-23 position $R^1$ is hydrogen to the organism responsible for said infection or infestation or to the location thereof.

* * * * *

UNITED STATES PATENT AND TRADEMARK OFFICE
CERTIFICATE OF CORRECTION

PATENT NO. : 5,057,498

DATED : October 15, 1991

INVENTOR(S) : Christopher J. Dutton et al.

It is certified that error appears in the above-identified patent and that said Letters Patent is hereby corrected as shown below:

In the Abstract, line 10 - "-$CH_2$13," should read -- -$CH_2$- --.

At Column 7, line 15, "Capillalria" should read -- Capillaria --.

At Column 9, lines 7, 8 - "4'-(alpha-L-oleandroxyl)-L-oleandroxyloxy," should read -- 4'-(alpha-L-oleandrosyl)-L-oleandrosyloxy, --.

At Column 9, line 29, add "Pharmamedia (15 g), ardamine pH (5 g) and calcium carbonate (2 g)" after "(20 g)".

At Column 9, line 66 - "4'-(alpha-L-oleandroxyl)-L-oleandrosyloxyl," should read -- 4'-(alpha-L-oleandrosyl)-L-oleandrosyloxyl, --.

At Column 10, line 41, "5-benzoyl N-acetyl" should read -- S-benzoyl N-acetyl --.

UNITED STATES PATENT AND TRADEMARK OFFICE
CERTIFICATE OF CORRECTION

PATENT NO. : 5,057,498
DATED : October 15, 1991
INVENTOR(S) : Christopher J. Dutton et al.

It is certified that error appears in the above-identified patent and that said Letters Patent is hereby corrected as shown below:

At Column 10, line 41 - "cycteamine" should read -- cysteamine --.

At Column 10, line 63 - "cystamine" should read -- cysteamine --.

At Column 12, lines 26, 27 - delete "alkoxy having one to four carbon atoms," (second occurrence).

At Column 13, lines 25, 26 - delete "alkoxy having one to four carbon atoms," (second occurrence).

Signed and Sealed this

Eleventh Day of October, 1994

Attest:

BRUCE LEHMAN

Attesting Officer

Commissioner of Patents and Trademarks